US009421157B2

(12) United States Patent
Dalko et al.

(10) Patent No.: US 9,421,157 B2
(45) Date of Patent: Aug. 23, 2016

(54) USE OF C-GLYCOSIDE DERIVATIVES AS PRO-DESQUAMATING ACTIVE AGENTS

(75) Inventors: Maria Dalko, Gif sur Yvette (FR); Christophe Boulle, Paris (FR); Dominique Bernard, Paris (FR)

(73) Assignee: L'OREAL, Paris (FR)

( * ) Notice: Subject to any disclaimer, the term of this patent is extended or adjusted under 35 U.S.C. 154(b) by 861 days.

(21) Appl. No.: 12/306,565

(22) PCT Filed: Jun. 29, 2007

(86) PCT No.: PCT/IB2007/052527
§ 371 (c)(1),
(2), (4) Date: Mar. 19, 2009

(87) PCT Pub. No.: WO2008/004165
PCT Pub. Date: Jan. 10, 2008

(65) Prior Publication Data
US 2010/0003236 A1 Jan. 7, 2010

Related U.S. Application Data

(60) Provisional application No. 60/832,943, filed on Jul. 25, 2006.

(30) Foreign Application Priority Data

Jul. 3, 2006 (FR) ..................................... 06 06016

(51) Int. Cl.
*C12Q 1/68* (2006.01)
*A61K 31/74* (2006.01)
*A61K 8/60* (2006.01)
*A61Q 5/00* (2006.01)
*A61Q 19/00* (2006.01)

(52) U.S. Cl.
CPC ............... *A61K 8/602* (2013.01); *A61Q 5/006* (2013.01); *A61Q 19/00* (2013.01); *A61Q 19/008* (2013.01); *A61K 2800/28* (2013.01); *A61K 2800/88* (2013.01)

(58) Field of Classification Search
None
See application file for complete search history.

(56) References Cited

U.S. PATENT DOCUMENTS

| | | |
|---|---|---|
| 3,915,300 A | 10/1975 | Gatley |
| 4,234,435 A | 11/1980 | Meinhardt et al. |
| 4,252,951 A | 2/1981 | Jackson et al. |
| 4,446,312 A | 5/1984 | Noyori et al. |
| 4,509,949 A | 4/1985 | Huang et al. |
| 4,708,753 A | 11/1987 | Forsberg |
| 4,919,179 A | 4/1990 | Chattopadhyay |
| 4,931,110 A | 6/1990 | McKenzie et al. |
| 4,983,382 A | 1/1991 | Wilmott et al. |
| 5,089,578 A | 2/1992 | Valint et al. |
| 5,129,972 A | 7/1992 | Riga et al. |
| 5,346,693 A | 9/1994 | Pilleux |
| 5,412,004 A | 5/1995 | Tachibana et al. |
| 5,492,426 A | 2/1996 | Gueret |
| 5,518,517 A | 5/1996 | Jahnke et al. |
| 5,607,921 A | 3/1997 | Bernard et al. |
| 5,789,385 A | 8/1998 | Anderson et al. |
| 5,811,487 A | 9/1998 | Schulz, Jr. et al. |
| 5,858,055 A | 1/1999 | Jahnke et al. |
| 6,099,870 A | 8/2000 | Cauwenbergh |
| 6,194,452 B1 | 2/2001 | Murad |
| 6,306,376 B1 | 10/2001 | Philippe |
| 6,328,495 B1 | 12/2001 | Gueret |
| 6,413,936 B1 | 7/2002 | Schmidt et al. |
| 6,484,731 B1 | 11/2002 | Lacout |
| 6,495,147 B1 | 12/2002 | Dumas et al. |
| 6,645,476 B1 | 11/2003 | Morschhäuser et al. |
| 6,987,128 B2 | 1/2006 | Dalko et al. |
| 7,049,300 B2* | 5/2006 | Dalko et al. ..................... 514/23 |
| 7,079,300 B1* | 7/2006 | Govyadinov et al. ......... 359/288 |
| 7,153,498 B2 | 12/2006 | Aubrun-Sonneville et al. |
| 7,666,847 B2 | 2/2010 | Houlmont et al. |
| 7,732,414 B2* | 6/2010 | Dalko et al. ..................... 514/23 |
| 8,088,399 B2* | 1/2012 | De Lacharriere et al. ... 424/401 |
| 2003/0044439 A1 | 3/2003 | Dobson, Jr. et al. |
| 2003/0124079 A1 | 7/2003 | Mougin et al. |
| 2003/0147830 A1* | 8/2003 | Phillips et al. ............ 424/70.14 |
| 2003/0152600 A1 | 8/2003 | Dalko et al. |
| 2004/0005342 A1 | 1/2004 | Bernerd |
| 2004/0048785 A1 | 3/2004 | Dalko et al. |
| 2004/0234464 A1 | 11/2004 | Herve |
| 2005/0002889 A1* | 1/2005 | Dalko et al. ............... 424/70.13 |
| 2005/0250708 A1 | 11/2005 | Trouille |
| 2006/0223763 A1 | 10/2006 | Dalko et al. |
| 2008/0003191 A1 | 1/2008 | Simonnet et al. |
| 2008/0008674 A1 | 1/2008 | Burnier et al. |
| 2008/0014162 A1* | 1/2008 | Willemin et al. ............ 424/70.1 |
| 2008/0014230 A1* | 1/2008 | Pineau et al. ................. 424/401 |
| 2008/0026020 A1 | 1/2008 | Willemin et al. |
| 2008/0226756 A1* | 9/2008 | Willemin et al. ............. 424/732 |
| 2009/0041691 A1* | 2/2009 | Candau et al. .................. 424/60 |
| 2009/0075935 A1* | 3/2009 | Bissey et al. ................... 514/54 |
| 2009/0274638 A1* | 11/2009 | Pineau et al. ................... 424/59 |
| 2010/0168055 A1* | 7/2010 | Laboureau et al. ............ 514/53 |
| 2010/0190742 A1* | 7/2010 | Breton et al. ................... 514/54 |

FOREIGN PATENT DOCUMENTS

| | | |
|---|---|---|
| DE | 27 03 185 A1 | 8/1978 |
| EP | 0 173 109 A2 | 3/1986 |

(Continued)

OTHER PUBLICATIONS

Jordan, Tamoxifen: A Most Unlikely Pioneering Medicine, Nature Review: Drug Discovery, vol. 2, Mar. 2003, p. 205.*

(Continued)

*Primary Examiner* — Reza Ghafoorian
(74) *Attorney, Agent, or Firm* — Oliff PLC

(57) ABSTRACT

A cosmetic use of at least one C-glycoside derivative in a composition comprising a physiologically acceptable medium, as a cosmetic agent for promoting the desquamation of the skin and/or the scalp and/or for stimulating epidermal renewal.

9 Claims, No Drawings

(56) References Cited

FOREIGN PATENT DOCUMENTS

| | | |
|---|---|---|
| EP | 0 216 479 A1 | 4/1987 |
| EP | 0 425 066 A1 | 5/1991 |
| EP | 0 487 404 A1 | 5/1992 |
| EP | 0 518 772 A1 | 12/1992 |
| EP | 0 518 773 A1 | 12/1992 |
| EP | 0 524 109 B1 | 6/1995 |
| EP | 0 667 145 A1 | 8/1995 |
| EP | 0 750 899 A2 | 1/1997 |
| EP | 0 771 795 A1 | 5/1997 |
| EP | 0 852 949 A2 | 7/1998 |
| EP | 1 069 142 | 1/2001 |
| EP | 0 895 779 B1 | 8/2003 |
| EP | 1 430 883 A1 | 6/2004 |
| EP | 1 466 590 A1 | 10/2004 |
| EP | 1 468 674 A1 | 10/2004 |
| EP | 1 473 024 A1 | 11/2004 |
| EP | 1 589 010 A1 | 10/2005 |
| FR | 2 609 397 A1 | 7/1988 |
| FR | 2 722 380 A1 | 1/1996 |
| FR | 2 756 735 A1 | 6/1998 |
| FR | 2 761 959 A1 | 10/1998 |
| FR | 2 768 623 A1 | 3/1999 |
| FR | 2 770 776 A1 | 5/1999 |
| FR | 2 773 324 A1 | 7/1999 |
| FR | 2 791 042 A1 | 9/2000 |
| FR | 2 792 618 A1 | 10/2000 |
| FR | 2 811 565 A1 | 1/2002 |
| FR | 2 811 993 A1 | 1/2002 |
| FR | 2 818 547 A1 | 6/2002 |
| FR | 2 818 646 A1 | 6/2002 |
| FR | 2 861 729 A1 | 5/2005 |
| FR | 2 867 684 A1 | 9/2005 |
| FR | 2 869 317 A1 | 10/2005 |
| FR | 2 876 283 A1 | 4/2006 |
| FR | 2 877 220 A1 | 5/2006 |
| GB | 2 156 799 | 10/1985 |
| JP | A-02-295912 | 12/1990 |
| WO | WO 93/04665 A1 | 3/1993 |
| WO | WO 96/19182 A1 | 6/1996 |
| WO | WO 96/19184 A1 | 6/1996 |
| WO | WO 98/44012 A1 | 10/1998 |
| WO | WO 99/10318 A1 | 3/1999 |
| WO | WO 99/22707 A1 | 5/1999 |
| WO | WO 99/24009 A1 | 5/1999 |
| WO | WO 99/32077 A1 | 7/1999 |
| WO | WO 00/68282 A1 | 11/2000 |
| WO | WO 01/03538 A1 | 1/2001 |
| WO | WO 01/79644 A1 | 10/2001 |
| WO | WO 00/31154 A1 | 6/2002 |
| WO | WO 02/43677 A2 | 6/2002 |
| WO | WO 02/43686 A2 | 6/2002 |
| WO | WO 02/43687 A2 | 6/2002 |
| WO | WO 02/43688 A2 | 6/2002 |
| WO | WO 02/43689 A2 | 6/2002 |
| WO | WO 02/44224 A2 | 6/2002 |
| WO | WO 02/44225 A2 | 6/2002 |
| WO | WO 02/44227 A2 | 6/2002 |
| WO | WO 02/44229 A1 | 6/2002 |
| WO | WO 02/44230 A2 | 6/2002 |
| WO | WO 02/44231 A1 | 6/2002 |
| WO | WO 02/44267 A2 | 6/2002 |
| WO | WO 02/44268 A1 | 6/2002 |
| WO | WO 02/44269 A1 | 6/2002 |
| WO | WO 02/44270 A2 | 6/2002 |
| WO | WO 02/44271 A2 | 6/2002 |
| WO | WO 02/051803 A2 | 7/2002 |
| WO | WO02/051828 * | 7/2002 ........... C07D 309/10 |
| WO | WO 02/051828 A2 | 7/2002 |
| WO | WO 03/018423 A1 | 3/2003 |
| WO | WO 2004/028483 A2 | 4/2004 |
| WO | WO 2004/073759 A1 | 9/2004 |
| WO | WO 2006/090307 * | 8/2006 ............... A61K 8/60 |
| WO | WO 2006/090307 A1 | 8/2006 |
| WO | WO 2006/128738 A1 | 12/2006 |
| WO | WO 2008/148966 A2 | 12/2008 |
| WO | WO 2009/034559 A2 | 3/2009 |

OTHER PUBLICATIONS

Schafer et al., Failure is an option: learning from unsuccessful proof-of-concept trials, Drug Discovery Today, vol. 13, Nos. 21/22, Nov. 2008.*

Horig et al., From bench to clinic and back: Perspective on the 1st IQPC Translational Research conference, Journal of Translational Medicine 2004, 2:44.*

Jan. 12, 2012 Office Action issued in U.S. Appl. No. 11/822,098.

Office Action issued in U.S. Appl. No. 11/822,160; mailed Oct. 27, 2010.

Office Action issued in U.S. Appl. No. 11/822,107; mailed Jun. 24, 2010.

Office Action issued in U.S. Appl. No. 11/822,098; mailed Jul. 13, 2010.

Egelrud et al., "Proteolytic Degradation of Desmosomes in Plantar Stratum Corneum Leads to Cell Dissociation in vitro," *Acta Derm Venereol.*, vol. 68, pp. 93-97, 1988.

Egelrud et al., "The Dependence of Detergent-Induced Cell Dissociation in Non-Palmo-Plantar Stratum Corneum on Endogenous Proteolysis," *J. Invest Dermatol.*, vol. 95, No. 4, pp. 456-459, Oct. 1990.

Egelrud et al., "A chymotrypsin-like proteinase that may be involved in desquamation in plantar stratum corneum," *Archives of Dermatological Research*, vol. 238, pp. 108-112, 1991.

Walsh et al., "Sugars protect desmosome and comeosome glycoproteins from proteolysis," *Archives of Dermatological Research*, vol. 283, pp. 174-179, 1991.

Brysk et al., "Glycoproteins modulate adhesion in terminally differentiated keratinocytes," *Cell and Tissue Research*, vol. 253, pp. 657-663, 1988.

Brysk et al., "Predesquamin Inhibits Desquamation," *Experimental Cell Research*, vol. 209, pp. 301-306, 1993.

Brysk et al., "Cohesion and desquamation of epidermal stratum corneum," *Prog. Histochem Cytochem.*, vol. 25, pp. 1-53, 1992.

Brysk et al., "Sensitivity of Desquamin to Proteolytic Degradtion," *Pathobiology*, vol. 59, pp. 109-112, 1991.

Vicanova et al., "Impaired desquamation in the in vitro reconstructed human epidermis," *Cell & Tissue Research*, vol. 286, pp. 115-122, 1996.

Simon et al., "Persistence of Both Peripheral and Non-Peripheral Comeodesmosomes in the Upper Stratum Corneum of Winter Xerosis Skin *Versus* only Peripheral in Normal Skin," *Journal of Investigative Dermatology*, vol. 116, No. 1, Jan. 2001.

Imokawa, Genji et al., "Decreased Level of Ceramides in Stratum Corneum of Atopic Dermatitis: An Etiologic Factor in Atopic Dry Skin?" The Journal of Investigative Dermatology, 1991, pp. 523-526, vol. 96.

Di Nardo, A. et al., "Ceramide and Cholesterol Composition of the Skin of Patients with Atopic Dermatitis", Acta Derm Venereol (Stockh), 1998, pp. 27-30, vol. 78.

Wilmer J. et al., "Cytokine Induction in Human Epidermal Keratinocytes Exposed to Contact Irritants and Its Relation to Chemical-Induced Inflammation in Mouse Skin," Journal of Investigative Dermatology, 1994, pp. 915-922, vol. 102.

Morisette, S.L. et al., "High-Throughput Crystallization: Polymorphs, Salts, Co-Crystals and Solvates of Pharmaceutical Solids," Advanced Drug Delivery Reviews, 2004, pp. 275-300, vol. 56.

Vippagunta, S.R. et al., "Crystalline Solids," Advanced Drug Delivery Reviews, 2001, pp. 3-26, vol. 48.

Allgaier, J., et al. "Synthesis and Characterization of Poly[1,4-isoprene-b-(ethyleneoxide)] and Poly[ethylene-co-propylene-b-(ethylene oxide)] Block Copolymers," Macromolecules, 1997, pp. 1582-1586, vol. 30, No. 6.

Morishima, Y. "Self-Assembling Amphiphilic Polyelectrolytes and Their Nanostructures," Chinese Journal of Polymer Science, 2000, pp. 323-336, vol. 18, No. 40.

(56) References Cited

OTHER PUBLICATIONS

Noda, T., et al. "Micelle Formation of Random Copolymers of Sodium 2-(Acrylamido)-2-methylpropanesulfonate and a Nonionic Surfactant Macromonomer in Water as Studied by Fluorescence and Dynamic Light Scattering," Macromolecules, 2000, pp. 3694-3704, vol. 33, No. 10.
Noda, T., et al. "Solution Properties of Micelle Networks Formed by Nonionic Surfactant Moieties Covalently Bound to a Polyelectrolyte: Salt Effects on Rheological Behavior," Langmuir, 2000, pp. 5324-5332, vol. 16, No. 12.
Noda, T., et al. "Stimuli-Responsive Amphiphilic Copolymers of Sodium 2-(Acrylamido)-2-Methylpropanesulfonate and Associative Macromonomers," Polymer Preprints, 1999, pp. 220-221, vol. 40, No. 2.
WordNet Search 3.0, "Prevent," Nov. 14, 2007.
YourDictionary.com, "Calmative," Jan. 28, 2010.
Merriam-Webster Online Dictionary, "Derivative," Jul. 15, 2009.
MayoClinic, "Hair Loss," Feb. 12, 2010.
The Merck Manual of Diagnostics and Therapy, Seventeenth Edition, 1999, pp. 788-791.
U.S. Office Action issued Dec. 29, 2009 in related U.S. Appl. No. 11/822,115.
U.S. Office Action issued Dec. 11, 2008 in related U.S. Appl. No. 11/822,114.
U.S. Office Action issued Sep. 30, 2009 in related U.S. Appl. No. 11/822,114.
U.S. Office Action issued Feb. 4, 2010 in related U.S. Appl. No. 11/822,160.
U.S. Office Action issued Jan. 7, 2010 in related U.S. Appl. No. 11/822,098.
U.S. Office Action issued May 13, 2009 in related U.S. Appl. No. 11/783,410.
U.S. Office Action issued Feb. 3, 2010 in related U.S. Appl. No. 11/783,410.
U.S. Office Action issued Jun. 24, 2009 in related U.S Appl. No. 11/783,411.
U.S. Office Action issued Feb. 3, 2010 in related U.S. Appl. No. 11/783,411.
International Search Report issued Dec. 10, 2007 in Application No. PCT/FR2007/051587.
French Search Report issued in French Application No. 0606021, Feb. 15, 2007.
French Search Report issued in French Application No. 0606025, Feb. 22, 2007.
French Search Report issued in French Application No. 0606015, May 6, 2005.
French Search Report issued in French Application No. 0606023, Apr. 4, 2007.
French Search Report issued in French Application No. 0651269, Dec. 15, 2006.
May 19, 2011 Restriction and Election of Species Requirement issued in U.S. Appl. No. 12/306,566.
Sep. 1, 2011 Office Action issued in U.S. Appl. No. 11/822,160.
Held, E. et al., "Effect of different moisturizers on SLS-irritated human skin", Contact Dermatitis, 2001, vol. 44, pp. 299-234.
MayoClinic.com, "Dry Skin", http://www.mayoclinic.com/health/dry-skin/DSOO560; last viewed Aug. 25, 2011, seven pages.
Third Parties Observations issued in European Patent Application No. 07301199.1 dated Nov. 11, 2011.

Brhat Nighantu Ratnakara (Saligramanighantubhusanam)—Compiled by Gangāvisnu Śrikrsna Dāsa ,Translated by Sri Dattarama Srikrsnalala Mathura; vol.-4 (Part VII), edn. 1997, Khemaraja Srikrsnadas Prakasana, Mumbai-4 [This book contains back references from 1000 B.C. to 20$^{th}$ century] p. 370 Formulation ID: RS/4798 Formulation Name: Śatapatrīgunāh.
Sodhala; Sodhalanighantauh-(Nāmasamgraha Va Gunasamgraha) Edited by P.V. Sharma, Oriental Institute, Baroda, Edn 1$^{st}$ 1978 p. 136 Formulation ID: RG9/396B Formulation Name: Satapatrika Lepa.
Rasatantrasārah Evam Siddhaprayogasamgrahah;-part II; Krishan Gopal Ayurveda Bhawan;Edn 8$^{th}$; 1990 [This book contains back references from 1000 B.C. to 20$^{th}$ century] p. 538 Formulation ID: RS21 / 688 Formulation Name: Akasira Dimaga Taila.
Rasatantrasārah Evam Siddhaprayogasamgrahah;-part II; Krishan Gopal Ayurveda Bhawan; Edn 8$^{th}$; 1990 [This book contains back references from 1000 B.C. to 20$^{th}$ century] p. 485-486 Formulation ID: RS21/600 Formulation Name: Pandeya Udvartana.
Jul. 18, 2012 Office Action issued in U.S. Appl. No. 12/306,566.
Campoccia et al., "Semisynthetic Resorbable Materials from Hyaluronan Esterification", Biomaterials 19; 1998; 2101-2127.
Stern et al., "Hyaluronan fragments: An information-rich system", European Journal of Cell Biology; vol. 85; 2006; pp. 699-715.
Braga et al., "Making crystals from crystals: a green route to crystal engineering and polymorphism," Chem. Commun., 2005; 3635-3645.
General Chemistry Online Dictionary, "lipid"; also available at http://antoine.frostburg.edu/chem/senese/101/glossary/l.shtml; last accessed Apr. 25, 2012.
SciFinder, "Jojoba Oil"; last accessed Apr. 25, 2012.
May 3, 2012 Office Action issued in U.S. Appl. No. 11/822,160.
U.S. Appl. No. 12/192,698 in the name of Bissey et al., filed Aug. 15, 2008.
U.S. Appl. No. 12/649,366 in the name of Laboureau et al., filed Dec. 30, 2009.
U.S. Appl. No. 12/704,978 in the name of Breton et al., filed Feb. 12, 2010.
U.S. Appl. No. 11/822,098 in the name of Pineau et al., Jul. 2, 2007.
U.S. Appl. No. 11/822,160 in the name of Willemin et al., filed Jul. 2, 2007.
U.S. Appl. No. 12/306,566 in the name of Pineau et al., filed Feb. 26, 2009.
Hilda Butler, "Poucher's Perfumes, Cosmetics and Soaps," 2000, Kluwer Academic Publishers, 10$^{th}$ Edition, pp. 403-405.
The Merriam-Webster Online Dictionary, obtained online at: http://www.merriam-webster.com/dictionary/prevent, downloaded on Jan. 24, 2012, 2 pages.
The Merriam-Webster Online Dictionary, obtained online at: http://www.merriam-webster.com/dictionary/cure, downloaded on Jan. 24, 2012, 2 pages.
The Merriam-Webster Online Dictionary, obtained online at: http://www.merriam-webster.com/dictionary/derivative, downloaded on Jul. 5, 2008, 1 page.
Wermuth, Drug Discovery Today, 2006, vol. 11, Nos. 7/8, pp. 348-354.
Jan. 30, 2012 Office Action issued in U.S. Appl. No. 12/306,566.
Jul. 31, 2013 Office Action issued in U.S. Appl. No. 12/306,566.
Apr. 15, 2014 Office Action issued in U.S. Appl. No. 12/306,566.

\* cited by examiner

USE OF C-GLYCOSIDE DERIVATIVES AS PRO-DESQUAMATING ACTIVE AGENTS

The invention relates to the cosmetic use of at least one C-glycoside derivative in a composition, especially a cosmetic composition, comprising a physiologically acceptable medium, as an agent for promoting desquamation of the skin and/or the scalp and/or for stimulating epidermal renewal.

The C-glycoside derivative according to the present invention may be used for cosmetic and/or therapeutic purposes, provided that it is used as an active agent for stimulating desquamation, also known as a pro-desquamating active agent.

Desquamation is a natural phenomenon associated with the fact that the epidermis, which constitutes the upper layer of the skin, is in constant regeneration.

The epidermis consists of several layers of cells, the deepest of which is the basal layer consisting of undifferentiated cells. Over time, these cells differentiate and migrate towards the surface of the epidermis, forming the various layers thereof, until they form at the surface of the epidermis the corneocytes, which are dead cells that become removed by desquamation. This surface loss is compensated for by the migration of cells from the basal layer to the surface of the epidermis. This constitutes a perpetual renewal of the skin.

The corneocytes are mainly composed of a fibrous matrix containing cytokeratins, surrounded by a very strong structure 15 nm thick, known as the horny or cornified envelope. The stacking of these corneocytes constitutes the horny layer, which is responsible for the barrier function of the epidermis. During the normal process of desquamation, the uppermost corneocytes become detached from the surface of the epidermis.

Intercellular structures derived from desmosomes, known as corneosomes or corneodesmosomes, have been described in the horny layer. Recent studies have shown their major importance in intercorneocytic cohesion and also in the desquamation process.

The gradual appearance of fragments of desmosomal proteins during the differentiation and also the ultrastructural changes of the desmosome put research workers on the track of enzymes responsible for these changes. The first, Egelrud and Lundström (Egelrud, Hofer et al. 1988 *Acta Derm. Venereol.* 68:93-97; Egelrud and Lundström1990, *J. Invest. Dermatol.* 95: 456-459; Egelrud and Lundström, 1991, *Arch. Dermatol. Res.* 283: 108-112), have demonstrated in the stratum corneum the existence of protease activities of "trypsin-like" and above all "chymotrypsin-like" type associated with desquamation. Several cysteine proteases and aspartic acid proteases are now assumed to be involved in this process: "stratum corneum thiol protease" (SCTP), cathepsin E and cathepsin D.

Walsh and Chapman (Walsh and Chapman, 1991; *Arch. Dermatol Res.* 283: 174-179) have shown that desquamation is the result of the action of at least two classes of enzymes on the intercorneocytic bonds. They have observed that the proteases cannot act alone and that a prior action of glycosidases that demask the sites of proteolysis is necessary. The experiments they performed confirmed that glycoproteins play a major role in cohesion. One particular glycoprotein has been described in relation with desquamation, and named desquamine. It is a 40 kDa glycoprotein located in the upper part of the stratum corneum, and which was isolated by Brysk et al. (Brysk et al. 1988; *Cell Tissue Res.* 253: 657-663). Its precursor, predesquamine (600 kDa), is believed to be located in the deep layers the stratum corneum and in the stratum granulosum (SG). M. Brysk showed, by using the desquamation model of T. Egelrud, that this precursor inhibits desquamation in a dose-dependent manner at very low concentrations, of nanomolar order (Brysk et al., 1993; *Exp. Cell Res.* 209: 301-306). It is thus thought to play an important role in blocking early desquamation. Its degradation in the SG/stratum corneum interzone and in the upper part of the stratum corneum generates desquamine, which in turn is believed to modify desquamation (Brysk and Rajaraman, 1992; *Prog. Histochem. Cytochem.* 25: 1-53). Desquamine is capable in vitro of causing haemagglutinations, which clearly proves its nature as an endogenous lectin. It is not competitively inhibited until sugar concentrations of millimolar order, whereas the other lectins are competitively inhibited for concentrations below 50 micromolar (Brysk et al., 1988). This lectin bonds the amino-sugars of adjacent cells by bridging. The use of an anti-desquamine monoclonal antibody for inhibiting the in vitro reaggregation of the corneocytes demonstrates the possible role of desquamine in cohesion.

Reaggregation is also inhibited by the addition of amino-sugars that bind to the endogenous lectins and by the addition of exogenous lectins specific for the amino-sugars, which bind the ligand (Brysk et al. 1988). Some of the these sugars have been claimed as pro-desquamating active agents. Finally, desquamine is resistant in vitro to the majority of the proteases described in the stratum corneum. This situation is reinforced in vivo, since its presence, in the lipid mortar of the spaces, protects its sites of enzymatic cleavage (Brysk et al., 1991; Pathobiology 59: 109-112).

The present invention is more particularly focused on treating the signs associated with desquamation disorders.

Deregulations of desquamation are increasingly well described at the molecular level and are associated with veritable pathologies of the type such as ichthyosis, psoriasis, atopic dermatitis and xerosis, for example, or with abnormal skin aspects.

Thus, in a certain number of situations, it may be desired to stimulate this desquamation mechanism in order to promote epidermal renewal, to attenuate surface irregularities and to make the skin smooth, or to promote the cleansing action and the removal of dead cells at the surface of the body.

In certain physiological conditions, thickening of the horny layer is also observed, which it is desired to limit, for example in the case of calluses or after exposure to sunlight.

In certain skin disorders, the desquamation becomes visible and large squamae comprising numerous corneocytes are removed.

In the field of acne, the accumulation of a keratinous plug (which may be removed by the activity of proteases) blocking the pores is one of the reasons for the appearance of comedones.

The appearance of dandruff is another example of a desquamation defect in which the squamae are abnormally visible.

Genetic defects at the level of proteases and of protease inhibitors are also associated with the appearance of hyperkeratotic or ichthyosic phenotypes.

The impaired desquamation that is generally present in reconstructed epidermides (Vicanova, Mommaas et al. 1996) also represents a proteolytic defect.

Certain pathological skin types may also benefit from pro-desquamating treatment. Among these pathologies, mention is made of Netherton's syndrome, Papillon-Lefèvre syndrome and more generally ichthyoses of genetic origin and also psoriasis or atopic dermatitis.

In the field of normal but impaired skin in which there is deregulation of desquamation, mention may be made of various xeroses (Simon et al., 2001; *J. Invest. Dermatol.* 116: 23-30), whether they are senile or winter-related, associated with the onset of the menopause or with the exaggerated use of certain detergents.

Thus, the present patent application is also directed towards desquamation disorders that can be remedied by means of solutions belonging to the field of cosmetics. In particular, in this respect, means may be sought for homogenizing the skin relief, for removing surface roughness to produce a smoothing effect, for improving the radiance of the complexion, for improving the staying power of makeup, for improving the efficacy of peeling treatments or for preparing the skin before the application of a self-tanning agents such as dihydroxyacetone (DHA).

Certain cosmetic agents are known to promote desquamation, i.e. the removal of "dead" cells at the surface of the horny layer of the epidermis. In this respect, mention may be made especially of α-hydroxy acids (AHAs), for instance lactic acid or glycolic acid, or β-hydroxy acids (BHAs), for instance salicylic acid. However, these desquamating agents may be criticized for being liable to cause undesirable local irritation.

There is thus a need to find pro-desquamating agents that can be implemented for their use against the abovementioned skin disorders, whether they are of dermatological nature or correspond more to concerns of a cosmetic nature also mentioned above, and free of the drawbacks described previously.

The inventors have discovered, surprisingly, that certain C-glycoside derivatives are advantageous in precisely this respect.

Sugars and sugar derivatives are products that have already been exploited for various purposes for the formulation of cosmetic compositions intended either for skincare or for caring for and/or washing keratin fibres.

Among these sugars, C-glycoside derivatives prove to be most particularly advantageous. Thus, certain C-glycoside derivatives have demonstrated advantageous biological properties, in particular for combating ageing of the epidermis and/or dryness of the skin. Such compounds are especially described in document WO 02/051 828.

The invention results more particularly from the observation by the inventors that C-glycoside derivatives show pro-desquamating properties.

Thus, according to one of its aspects, the invention relates to the cosmetic use of at least one C-glycoside derivative in a composition, especially a cosmetic composition, comprising a physiologically acceptable medium, as a cosmetic agent for promoting desquamation of the skin and/or the scalp and/or for stimulating epidermal renewal.

Such a composition is more particularly useful for improving the appearance and/or texture of the skin and/or the scalp.

According to one of its advantages, a composition according to the invention shows desquamating properties without inducing local irritation.

In particular, the present invention relates to the cosmetic use of at least one C-glycoside derivative in a composition, especially a cosmetic composition, comprising a physiologically acceptable medium, the said composition being intended for combating keratosis and imperfections of acne-prone greasy skin, for combating the formation of dandruff, for homogenizing the skin relief, for removing surface roughness to afford a smoothing effect, for reducing surface irregularities and the skin's microrelief, for improving the radiance of the complexion, for improving the staying power of makeup, for improving the efficacy of peeling treatments, or for preparing the skin before the application of a self-tanning agent such as dihydroxyacetone (DHA) and/or for improving the result of a skin treatment with stratum corneum colorants such as dihydroxyacetone (DHA).

More generally, it is understood that the cosmetic use according to the present invention makes it possible to improve the appearance and/or texture of the skin and/or the scalp.

As regards greasy skin, this is often associated with a desquamation defect, and with a thick skin grain. Furthermore, the excess sebum may serve as a support for the anarchic growth of saprophytic bacterial flora (in particular *Propionibacterium acnes* and *Pityrosporum ovale*), and cause the appearance of comedones and/or acne scars. These acne scars are another cutaneous sign of greasy skin that may advantageously be combated by means of the use of a C-glycoside according to the present invention.

The invention also relates to cosmetic processes for treating the skin and/or its appendages, for the purpose of stimulating desquamation and/or exfoliation and/or cell renewal, and to compositions for implementing them.

According to another of its aspects, a subject of the invention is the use of at least one C-glycoside derivative for the preparation of a composition for preventing and/or treating signs associated with desquamation disorders.

In particular, the invention also relates to the use of at least one C-glycoside derivative for the preparation of a composition for preventing and/or treating skin and/or scalp disorders linked to deregulation of desquamation, especially when it is associated with the production of a thick horny layer and/or with abnormal desquamation.

Many skin pathologies are characterized by the production of a thickened horny layer and by abnormal desquamation, i.e. hyperkeratosis. This may occur on any anatomical region of skin and in very varied clinical contexts. Its physiopathological substratum and its cause are varied.

Advantageously, the C-glycoside derivatives in accordance with the invention make it possible to promote desquamation of the skin and/or to stimulate epidermal renewal and thus, more particularly, to treat skin and/or scalp pathologies that are characterized by the production of a thickened horny layer and/or by abnormal desquamation.

Consequently, according to another of its aspects, the present invention also relates to the use of a C-glycoside derivative for the preparation of a composition for treating skin and/or scalp pathologies characterized by the production of a thickened horny layer and/or by abnormal desquamation.

As non-limiting illustrations of these skin and/or scalp disorders associated with deregulation of desquamation, mention may be made, in the context of the present invention, of:

xerosis,
acne,
hyperkeratosis,
psoriasis,
atopy,
ichthyosis, and
certain benign or malignant tumour lesions.

According to another of its aspects, the present invention relates to a cosmetic treatment process for promoting desquamation and/or for stimulating epidermal renewal, characterized in that it comprises the application to the skin and/or the scalp of a composition comprising, in a physiologically acceptable medium, at least one C-glycoside derivative.

Advantageously, the cosmetic treatment process is suitable for skin displaying keratosis, acne-prone greasy skin, skin with rough areas or skin with a thick skin grain.

Another subject of the invention is a cosmetic treatment process for improving the radiance of the complexion and/or for reducing surface irregularities of the skin and/or of mucous membranes, characterized in that at least one C-glycoside derivative, or a composition containing it, is applied to the skin or the mucous membranes.

For the implementation of this process, the C-glycoside derivative or the composition containing it may be applied to any area of skin or of its appendages, especially of the face, the neckline or the hands, or to the lips, in order to attenuate visible and/or tactile skin irregularities, for example to attenuate scars, to make the surface smooth and/or to remove dead skin especially from the lips.

According to another embodiment, the invention relates to a cosmetic process for promoting desquamation of the skin and/or mucous membranes, comprising at least one step (i) of preparing the skin for a peeling treatment, which consists in applying to the areas to be treated at least one C-glycoside derivative, at least at a concentration lower than that resulting in desquamation, and (ii) a subsequent step comprising the application of at least one desquamating agent at a concentration suitable for causing desquamation. A step of removing the desquamating agent(s) by rinsing will then be performed.

Advantageously, step (i) may be repeated with increasing concentrations of C-glycoside. These concentrations will be adapted by a person skilled in the art as a function of the desired effect and of the intended number of applications, but will generally be less than 10%. It may be possible, for example, to use a first concentration of about 2%, and then one or more successive applications with a concentration of about 4%, and then 6% or 8% by weight.

According to another of its aspects, the invention relates to a cosmetic process for treating keratin materials, which consists in applying at least two components:
a first component comprising at least one C-glycoside derivative or a composition containing it, especially as defined below,
a second component comprising at least one agent chosen from proteases, lipases and glycosidases,
these two components being applied simultaneously, in combination or sequentially to the skin, mucous membranes or the scalp.

According to one particular embodiment, these two components may be formulated in different compositions.

Advantageously, the second component will comprise at least one protease, involved in desquamation.

Agents chosen from moisturizers, agents that reduce or inhibit the activity of harmful proteases, agents that stimulate epidermal differentiation and anti-seborrhoeic agents may advantageously be present in the first and/or second component.

Another subject of the invention is the use of at least one C-glycoside derivative as defined hereinbelow, for the preparation of reconstructed skin.

The invention thus relates to a process for prolonging the lifetime of reconstructed skin in vitro, and more particularly reconstructed epidermides.

According to one of the embodiments, the reconstructed epidermis may be treated daily with low concentrations of a C-glycoside derivative such as C-β-D-xylopyranoside-2-hydroxypropane and derivatives thereof, in order to promote regular desquamation similar to that observed in the case of healthy skin in vivo.

According to another embodiment variant, the C-glycoside derivative, especially C-β-D-xylopyranoside-2-hydroxypropane may be spot-applied to a reconstructed epidermis, at a high dose similar to that of a peeling treatment, i.e. about 20% to 40% by weight relative to the weight of the composition, and then removed by rinsing. This process makes it possible to remove the constituted horny layer or a part thereof whose accumulation may be harmful to the survival of the keratinocytes.

C-Glycoside Derivatives

A C-glycoside derivative that is suitable for use in the invention may be a compound of general formula (I) below:

in which:
R represents:
a saturated $C_1$-$C_{20}$ and in particular $C_1$-$C_{10}$ or unsaturated $C_2$-$C_{20}$ and in particular $C_2$-$C_{10}$ linear alkyl radical, or a saturated or unsaturated, branched or cyclic $C_3$-$C_{20}$ and in particular $C_3$-$C_{10}$ alkyl radical;
a saturated $C_1$-$C_{20}$ and in particular $C_1$-$C_{10}$ or unsaturated $C_2$-$C_{20}$ linear, and in particular $C_2$-$C_{10}$, or saturated or unsaturated, branched or cyclic $C_3$-$C_{20}$ and in particular $C_3$-$C_{10}$ linear hydrofluoroalkyl or perfluoroalkyl radical;
the hydrocarbon-based chain constituting the said radicals possibly being, where appropriate, interrupted with 1, 2, 3 or more heteroatoms chosen from:
an oxygen,
a sulfur,
a nitrogen, and
a silicon,
and possibly being optionally substituted with at least one radical chosen from:
—$OR_4$,
—$SR_4$,
—$NR_4R_5$,
—$COOR_4$,
—$CONR_4R_5$,
—CN,
a halogen atom,
a $C_1$-$C_6$ hydrofluoroalkyl or perfluoroalkyl radical, and/or
a $C_3$-$C_8$ cycloalkyl radical,
with $R_4$ and $R_5$ possibly representing, independently of each other, a hydrogen atom or a saturated $C_1$-$C_{30}$ and in particular $C_1$-$C_{12}$ or unsaturated $C_2$-$C_{30}$ linear, and in particular $C_2$-$C_{12}$, or a saturated or unsaturated, branched or cyclic $C_3$-$C_{30}$ and in particular $C_3$-$C_{12}$ alkyl, perfluoroalkyl or hydrofluoroalkyl radical; or a $C_6$-$C_{10}$ aryl radical,
X represents a radical chosen from the groups:

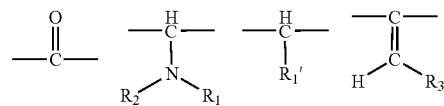

with $R_1$, $R_2$ and $R_3$ representing, independently of each other, a hydrogen atom or a radical R, with R as defined above, and R'$_1$ represents a hydrogen atom, an —OH group or a radical R as defined above, R$_1$ possibly also denoting a C$_6$-C$_{10}$ aryl radical;

S represents a monosaccharide or a polysaccharide comprising up to 20 sugar units and in particular up to 6 sugar units, in pyranose and/or furanose form and of L and/or D series, the said mono- or polysaccharide possibly being substituted with a mandatorily free hydroxyl group, and optionally one or more optionally protected amine function(s), and the bond S—CH$_2$—X represents a bond of C-anomeric nature, which may be α or β, and also the cosmetically acceptable salts thereof, the solvates thereof such as hydrates, and the isomers thereof.

In the context of the present invention, the term "halogen" means chlorine, fluorine or bromine.

The term "aryl" denotes an aromatic ring such as phenyl, optionally substituted with one or more C$_1$-C$_4$ alkyl radicals.

The term "C$_3$-C$_8$ cycloalkyl" denotes an aliphatic ring containing from 3 to 8 carbon atoms, for example including cyclopropyl, cyclopentyl and cyclohexyl.

Among the alkyl groups that are suitable for use in the invention, mention may be made especially of methyl, ethyl, isopropyl, n-propyl, n-butyl, t-butyl, isobutyl, sec-butyl, pentyl, n-hexyl, cyclopropyl, cyclopentyl, cyclohexyl and allyl groups.

According to one embodiment of the invention, it is possible to use a C-glycoside derivative corresponding to formula (I) for which S may represent a monosaccharide or a polysaccharide containing up to 6 sugar units, in pyranose and/or furanose form and of L and/or D series, the said monosaccharide or polysaccharide containing at least one hydroxyl function that is mandatorily free and/or optionally one or more amine functions that are mandatorily protected, X and R otherwise retaining all the definitions given above.

Advantageously, a monosaccharide of the invention may be chosen from D-glucose, D-galactose, D-mannose, D-xylose, D-lyxose, L-fucose, L-arabinose, L-rhamnose, D-glucuronic acid, D-galacturonic acid, D-iduronic acid, N-acetyl-D-glucosamine and N-acetyl-D-galactosamine, and advantageously denotes D-glucose, D-xylose, N-acetyl-D-glucosamine or L-fucose, and in particular D-xylose.

More particularly, a polysaccharide of the invention containing up to 6 sugar units may be chosen from D-maltose, D-lactose, D-cellobiose, D-maltotriose, a disaccharide combining a uronic acid chosen from D-iduronic acid and D-glucuronic acid with a hexosamine chosen from D-galactosamine, D-glucosamine, N-acetyl-D-galactosamine and N-acetyl-D-glucosamine, an oligosaccharide containing at least one xylose advantageously chosen from xylobiose, methyl-β-xylobioside, xylotriose, xylotetraose, xylopentaose and xylohexaose and especially xylobiose, which is composed of two xylose molecules linked via a 1-4 bond.

More particularly, S may represent a monosaccharide chosen from D-glucose, D-xylose, L-fucose, D-galactose and D-maltose, especially D-xylose.

According to another embodiment of the invention, it is possible to use C-glycoside derivatives corresponding to formula (I) for which X represents a group chosen from —CO—, —CH(OH)—, —CH(NR$_1$R$_2$)— and —CH(R)—, in particular —CO—, —CH(OH)—, —CH(NH$_2$)—, —CH(NHCH$_2$CH$_2$CH$_2$OH)—, —CH(NHPh)- and —CH(CH$_3$)—, and more particularly a —CO—, —CH(OH)— or —CH(NH$_2$)— group, and preferentially a —CH(OH)— group, S and R otherwise conserving all of the definitions given above.

According to another embodiment of the invention, it is possible to use a C-glycoside derivative corresponding to formula (I) for which R represents a saturated C$_1$-C$_{20}$ and in particular C$_1$-C$_{10}$ or unsaturated C$_2$-C$_{10}$ and in particular C$_2$-C$_{10}$ linear alkyl radical, or a saturated or unsaturated, branched or cyclic C$_3$-C$_{20}$ and in particular C$_3$-C$_{10}$ alkyl radical; and optionally substituted as described above, S and X otherwise conserving all the definitions given above. Preferably, R denotes a linear C$_1$-C$_4$ and especially C$_1$-C$_3$ radical, optionally substituted with —OH, —COOH or —COOR"$_2$, R"$_2$ being a saturated C$_1$-C$_4$ alkyl radical, especially ethyl.

Preferentially, R denotes an unsubstituted linear C$_1$-C$_4$ and especially C$_1$-C$_2$ alkyl radical, in particular ethyl.

Among the C-glycoside derivatives of formula (I) that are preferably used are those for which:

R represents a saturated C$_1$-C$_{20}$ and in particular C$_1$-C$_{10}$ or unsaturated C$_1$-C$_{20}$ and in particular C$_2$-C$_{10}$ linear alkyl radical, or a saturated or unsaturated, branched or Cyclic C$_3$-C$_{20}$ and in particular C$_3$-C$_{10}$ alkyl radical, optionally substituted as described above;

S represents a monosaccharide as described above;

X represents —CO—, —CH(OH)—, —CH(NR$_1$R$_2$)— or —CH(R)—, as defined above.

Preferably, a C-glycoside derivative of formula (I) is used, for which:

R denotes a linear C$_1$-C$_4$ and especially C$_1$-C$_3$ radical, optionally substituted with —OH, —COOH or —COOR"$_2$, R"$_2$ being a saturated C$_1$-C$_4$ alkyl radical, especially ethyl;

S represents a monosaccharide as described above;

X represents a group chosen from —CO—, —CH (OH)—, —CH(NH$_2$)—, —CH(NHCH$_2$CH$_2$CH$_2$OH)—, —CH(NHPh)- and —CH(CH$_3$)—, and more particularly a —CO—, —CH(OH)— or —CH(NH$_2$)— group, and in particular a —CH(OH)— group.

Preferentially, a C-glycoside derivative of formula (I) is used, for which:

R denotes an unsubstituted linear C$_1$-C$_4$ and especially C$_1$-C$_2$ alkyl radical, in particular ethyl;

S represents a monosaccharide as described above; especially D-glucose, D-xylose, N-acetyl-D-glucosamine or L-fucose, in particular D-xylose;

X represents a group chosen from —CO—, —CH(OH)— and —CH(NH$_2$)— and preferentially a CH(OH)— group.

The salts that are acceptable for the non-therapeutic use of the compounds described in the present invention comprise conventional non-toxic salts of the said compounds such as those formed from organic or inorganic acids. Examples that may be mentioned include the salts of mineral acids, such as sulfuric acid, hydrochloric acid, hydrobromic acid, hydriodic acid, phosphoric acid or boric acid. Mention may also be made of the salts of organic acids, which may comprise one or more carboxylic, sulfonic or phosphonic groups. They may be linear, branched or cyclic aliphatic acids or alternatively aromatic acids. These acids may also comprise one or more heteroatoms chosen from O and N, for example in the form of hydroxyl groups. Mention may be made especially of propionic acid, acetic acid, terephthalic acid, citric acid and tartaric acid.

When the compound of formula (I) comprises an acid group, neutralization of the acid group(s) may be performed with a mineral base, such as LiOH, NaOH, KOH, Ca(OH)$_2$, NH$_4$OH, Mg(OH)$_2$ or Zn(OH)$_2$; or with an organic base such as a primary, secondary or tertiary alkylamine, for example triethylamine or butylamine. This primary, secondary or tertiary alkylamine may comprise one or more nitrogen and/or oxygen atoms and may thus comprise, for example, one or more alcohol functions; mention may be made especially of amino-2-methyl-2-propanol, triethanolamine, dimethylamino-2-propanol or 2-amino-2-(hydroxymethyl)-1,3-propanediol. Mention may also be made of lysine or 3-(dimethylamino)propyl amine.

The solvates that are acceptable for the compounds described in the present invention comprise conventional solvates such as those formed during the final step of preparation of the said compounds due to the presence of solvents. Examples that may be mentioned include the solvates due to the presence of water or of linear or branched alcohols, for instance ethanol or isopropanol.

Among the C-glycoside derivatives of formula (I) used according to the invention, the ones that are most particularly considered are:

1. C-β-D-xylopyranoside-n-propan-2-one;
2. C-α-D-xylopyranoside-n-propan-2-one;
3. 1-[2-(3-hydroxypropylamino)propyl]-C-β-D-xylopyranose;
4. 1-[2-(3-hydroxypropylamino)propyl]-C-α-D-xylopyranose;
5. C-β-D-xylopyranoside-2-hydroxypropane;
6. C-α-D-xylopyranoside-2-hydroxypropane;
7. C-β-D-xylopyranoside-2-aminopropane;
8. C-α-D-xylopyranoside-2-aminopropane;
9. C-β-D-xylopyranoside-2-phenylaminopropane;
10. C-α-D-xylopyranoside-2-phenylaminopropane;
11. ethyl 3-methyl-4-(C-β-D-xylopyranoside)butyrate;
12. ethyl 3-methyl-4-(C-α-D-xylopyranoside)butyrate;
13. 6-(C-β-D-xylopyranoside)-5-ketohexanoic acid;
14. 6-(C-α-D-xylopyranoside)-5-ketohexanoic acid;
15. 6-(C-β-D-xylopyranoside)-5-hydroxyhexanoic acid;
16. 6-(C-α-D-xylopyranoside)-5-hydroxyhexanoic acid;
17. 6-(C-β-D-xylopyranoside)-5-aminohexanoic acid;
18. 6-(C-α-D-xylopyranoside)-5-aminohexanoic acid;
19. 6-(C-β-D-xylopyranoside)-5-phenylaminohexanoic acid;
20. 6-(C-α-D-xylopyranoside)-5-phenylaminohexanoic acid;
21. 1-(C-β-D-xylopyranoside)hexane-2,6-diol;
22. 1-(C-α-D-xylopyranoside)hexane-2,6-diol;
23. 5-(C-β-D-xylopyranoside)-4-ketopentanoic acid;
24. 5-(C-α-D-xylopyranoside)-4-ketopentanoic acid;
25. 5-(C-β-D-xylopyranoside)-4-hydroxypentanoic acid;
26. 5-(C-α-D-xylopyranoside)-4-hydroxypentanoic acid;
27. 5-(C-β-D-xylopyranoside)-4-aminopentanoic acid;
28. 5-(C-α-D-xylopyranoside)-4-aminopentanoic acid;
29. 5-(C-β-D-xylopyranoside)-4-phenylaminopentanoic acid;
30. 5-(C-α-D-xylopyranoside)-4-phenylaminopentanoic acid;
31. 1-(C-β-D-xylopyranoside)pentane-2,5-diol;
32. 1-(C-α-D-xylopyranoside)pentane-2,5-diol;
33. 1-(C-β-D-fucopyranoside)propan-2-one;
34. 1-(C-α-D-fucopyranoside)propan-2-one;
35. 1-(C-β-L-fucopyranoside)propan-2-one;
36. 1-(C-α-L-fucopyranoside)propan-2-one;
37. 1-(C-β-D-fucopyranoside)-2-hydroxypropane;
38. 1-(C-α-D-fucopyranoside)-2-hydroxypropane;
39. 1-(C-β-L-fucopyranoside)-2-hydroxypropane;
40. 1-(C-α-L-fucopyranoside)-2-hydroxypropane;
41. 1-(C-β-D-fucopyranoside)-2-aminopropane;
42. 1-(C-α-D-fucopyranoside)-2-aminopropane;
43. 1-(C-β-L-fucopyranoside)-2-aminopropane;
44. 1-(C-α-L-fucopyranoside)-2-aminopropane;
45. 1-(C-β-D-fucopyranoside)-2-phenylaminopropane;
46. 1-(C-α-D-fucopyranoside)-2-phenylaminopropane;
47. 1-(C-β-L-fucopyranoside)-2-phenylaminopropane;
48. 1-(C-α-L-fucopyranoside)-2-phenylaminopropane;
49. ethyl 3-methyl-4-(C-β-D-fucopyranoside)butyrate;
50. ethyl 3-methyl-4-(C-α-D-fucopyranoside)butyrate;
51. ethyl 3-methyl-4-(C-β-L-fucopyranoside)butyrate;
52. ethyl 3-methyl-4-(C-α-L-fucopyranoside)butyrate;
53. 6-(C-β-D-fucopyranoside)-5-ketohexanoic acid;
54. 6-(C-α-D-fucopyranoside)-5-ketohexanoic acid;
55. 6-(C-β-L-fucopyranoside)-5-ketohexanoic acid;
56. 6-(C-α-L-fucopyranoside)-5-ketohexanoic acid,
57. 6-(C-β-D-fucopyranoside)-5-hydroxyhexanoic acid;
58. 6-(C-α-D-fucopyranoside)-5-hydroxyhexanoic acid;
59. 6-(C-β-L-fucopyranoside)-5-hydroxyhexanoic acid;
60. 6-(C-α-L-fucopyranoside)-5-hydroxyhexanoic acid;
61. 6-(C-β-D-fucopyranoside)-5-aminohexanoic acid;
62. 6-(C-α-D-fucopyranoside)-5-aminohexanoic acid;
63. 6-(C-β-L-fucopyranoside)-5-aminohexanoic acid;
64. 6-(C-α-L-fucopyranoside)-5-aminohexanoic acid;
65. 1-(C-β-D-fucopyranoside)hexane-2,6-diol;
66. 1-(C-α-D-fucopyranoside)hexane-2,6-diol;
67. 1-(C-β-L-fucopyranoside)hexane-2,6-diol;
68. 1-(C-α-L-fucopyranoside)hexane-2,6-diol;
69. 5-(C-β-D-fucopyranoside)-4-ketopentanoic acid;
70. 5-(C-α-fucopyranoside)-4-ketopentanoic acid;
71. 5-(C-β-L-fucopyranoside)-4-ketopentanoic acid;
72. 5-(C-α-L-fucopyranoside)-4-ketopentanoic acid;
73. 5-(C-β-D-fucopyranoside)-4-hydroxypentanoic acid;
74. 5-(C-α-D-fucopyranoside)-4-hydroxypentanoic acid;
75. 5-(C-β-L-fucopyranoside)-4-hydroxypentanoic acid;
76. 5-(C-α-L-fucopyranoside)-4-hydroxypentanoic acid;
77. 5-(C-β-D-fucopyranoside)-4-aminopentanoic acid;
78. 5-(C-α-D-fucopyranoside)-4-aminopentanoic acid
79. 5-(C-β-L-fucopyranoside)-4-aminopentanoic acid;
80. 5-(C-α-L-fucopyranoside)-4-aminopentanoic acid;
81. 1-(C-β-D-fucopyranoside)pentane-2,5-diol;
82. 1-(C-α-D-fucopyranoside)pentane-2,5-diol;
83. 1-(C-β-L-fucopyranoside)pentane-2,5-diol;
84. 1-(C-α-L-fucopyranoside)pentane-2,5-diol;
85. 1-(C-β-D-glucopyranosyl)-2-hydroxypropane;
86. 1-(C-α-D-glucopyranosyl)-2-hydroxypropane;
87. 1-(C-β-D-glucopyranosyl)-2-aminopropane,
88. 1-(C-α-D-glucopyranosyl)-2-aminopropane;
89. 1-(C-β-D-glucopyranosyl)-2-phenylaminopropane;
90. 1-(C-α-D-glucopyranosyl)-2-phenylaminopropane;
91. ethyl 3-methyl-4-(C-α-D-glucopyranosyl)butyrate;
92. ethyl 3-methyl-4-(C-α-D-glucopyranosyl)butyrate;
93. 6-(C-β-D-glucopyranosyl)-5-ketohexanoic acid;
94. 6-(C-α-D-glucopyranosyl)-5-ketohexanoic acid;
95. 6-(C-β-D-glucopyranosyl)-5-hydroxyhexanoic acid;
96. 6-(C-α-D-glucopyranosyl)-5-hydroxyhexanoic acid;
97. 6-(C-β-D-glucopyranosyl)-5-aminohexanoic acid;
98. 6-(C-α-D-glucopyranosyl)-5-aminohexanoic acid;
99. 6-(C-β-D-glucopyranosyl)-5-phenylaminohexanoic acid;
100. 6-(C-α-D-glucopyranosyl)-5-phenylaminohexanoic acid;
101. 1-(C-β-D-glucopyranosyl)hexane-2,6-diol;
102. 1-(C-α-D-glucopyranosyl)hexane-2,6-diol;
103. 6-(C-β-D-glucopyranosyl)-5-ketopentanoic acid;
104. 6-(C-α-D-glucopyranosyl)-5-ketopentanoic acid;
105. 6-(C-β-D-glucopyranosyl)-5-hydroxypentanoic acid;
106. 6-(C-α-D-glucopyranosyl)-5-hydroxypentanoic acid;
107. 6-(C-β-D-glucopyranosyl)-5-aminopentanoic acid;
108. 6-(C-α-D-glucopyranosyl)-5-hydroxypentanoic acid;
109. 6-(C-β-D-glucopyranosyl)-5-phenylaminopentanoic acid;

110. 6-(C-α-D-glucopyranosyl)-5-phenylaminopentanoic acid;
111. 1-(C-β-D-glucopyranosyl)pentane-2,5-diol;
112. 1-(C-α-D-glucopyranosyl)pentane-2,5-diol;
113. 1-(C-β-D-galactopyranosyl)-2-hydroxypropane;
114. 1-(C-α-D-galactopyranosyl)-2-hydroxypropane;
115. 1-(C-β-D-galactopyranosyl)-2-aminopropane;
116. 1-(C-α-D-galactopyranosyl)-2-aminopropane;
117. 1-(C-β-D-galactopyranosyl)-2-phenylaminopropane;
118. 1-(C-α-D-galactopyranosyl)-2-phenylaminopropane;
119. ethyl 3-methyl-4-(β-D-galactopyranosyl)butyrate;
120. ethyl 3-methyl-4-(α-D-galactopyranosyl)butyrate;
121. 6-(C-β-D-galactopyranosyl)-5-ketohexanoic acid;
122. 6-(C-α-D-galactopyranosyl)-5-ketohexanoic acid;
123. 6-(C-β-D-galactopyranosyl)-5-hydroxyhexanoic acid;
124. 6-(C-α-D-galactopyranosyl)-5-hydroxyhexanoic acid;
125. 6-(C-β-D-galactopyranosyl)-5-aminohexanoic acid;
126. 6-(C-α-D-galactopyranosyl)-5-aminohexanoic acid;
127. 6-(C-β-D-galactopyranosyl)-5-phenylaminohexanoic acid;
128. 6-(C-α-D-galactopyranosyl)-5-phenylaminohexanoic acid;
129. 1-(C-β-D-galactopyranosyl)hexane-2,6-diol;
130. 1-(C-α-D-galactopyranosyl)hexane-2,6-diol;
131. 6-(C-β-D-galactopyranosyl)-5-ketopentanoic acid;
132. 6-(C-α-D-galactopyranosyl)-5-ketopentanoic acid;
133. 6-(C-β-D-galactopyranosyl)-5-hydroxypentanoic acid;
134. 6-(C-α-D-galactopyranosyl)-5-hydroxypentanoic acid;
135. 6-(C-β-D-galactopyranosyl)-5-aminopentanoic acid;
136. 6-(C-α-D-galactopyranosyl)-5-aminopentanoic acid;
137. 6-(C-β-D-galactopyranosyl)-5-phenylaminopentanoic acid;
138. 6-(C-α-D-galactopyranosyl)-5-phenylaminopentanoic acid;
139. 1-(C-β-D-galactopyranosyl)pentane-2,6-diol;
140. 1-(C-α-D-galactopyranosyl)pentane-2,6-diol;
141. 1-(C-β-D-fucofuranosyl)propan-2-one;
142. 1-(C-α-D-fucofuranosyl)propan-2-one;
143. 1-(C-β-L-fucofuranosyl)propan-2-one;
144. 1-(C-α-L-fucofuranosyl)propan-2-one;
145. 3'-(acetamido-C-β-D-glucopyranosyl)propane-2'-one;
146. 3'-(acetamido-C-α-D-glucopyranosyl)propane-2'-one;
147. 1-(acetamido-C-β-D-glucopyranosyl)-2-hydroxylpropane;
148. 1-(acetamido-C-β-D-glucopyranosyl)-2-aminopropane;
149. 1-(acetamido-C-β-D-glucopyranosyl)-2-phenylaminopropane;
150. 1-(acetamido-C-α-D-glucopyranosyl)-2-phenylaminopropane;
151. ethyl 3-methyl-4-(acetamido-C-β-D-glucopyranosyl)butyrate;
152. ethyl 3-methyl-4-(acetamido-C-α-D-glucopyranosyl)butyrate;
153. 6-(acetamido-C-β-D-glucopyranosyl)-5-ketohexanoic acid;
154. 6-(acetamido-C-α-D-glucopyranosyl)-5-ketohexanoic acid;
155. 6-(acetamido-C-β-D-glucopyranosyl)-5-hydroxyhexanoic acid;
156. 6-(acetamido-C-α-D-glucopyranosyl)-5-hydroxyhexanoic acid;
157. 6-(acetamido-C-β-D-glucopyranosyl)-5-aminohexanoic acid;
158. 6-(acetamido-C-α-D-glucopyranosyl)-5-aminohexanoic acid;
159. 6-(acetamido-C-β-D-glucopyranosyl)-5-phenylaminohexanoic acid;
160. 6-(acetamido-C-α-D-glucopyranosyl)-5-phenylaminohexanoic acid;
161. 1-(acetamido-C-β-D-glucopyranosyl)hexane-2,6-diol;
162. 1-(acetamido-C-α-D-glucopyranosyl)hexane-2,6-diol;
163. 6-(acetamido-C-β-D-glucopyranosyl)-5-ketopentanoic acid;
164. 6-(acetamido-C-α-D-glucopyranosyl)-5-ketopentanoic acid;
165. 6-(acetamido-C-β-D-glucopyranosyl)-5-hydroxypentanoic acid;
166. 6-(acetamido-C-α-D-glucopyranosyl)-5-hydroxypentanoic acid;
167. 6-(acetamido-C-β-D-glucopyranosyl)-5-aminopentanoic acid;
168. 6-(acetamido-C-α-D-glucopyranosyl)-5-aminopentanoic acid;
169. 6-(acetamido-C-β-D-glucopyranosyl)-5-phenylaminopentanoic acid;
170. 6-(acetamido-C-α-D-glucopyranosyl)-5-phenylaminopentanoic acid;
171. 1-(acetamido-C-β-D-glucopyranosyl)pentane-2,5-diol;
172. 1-(acetamido-C-α-D-glucopyranosyl)pentane-2,5-diol.

As non-limiting illustrations of C-glycoside derivatives that are more particularly suitable for use in the invention, mention may be made especially of the following derivatives:

C-β-D-xylopyranoside-n-propan-2-one,
C-α-D-xylopyranoside-n-propan-2-one,
C-β-D-xylopyranoside-2-hydroxypropane,
C-α-D-xylopyranoside-2-hydroxypropane,
1-(C-β-D-fucopyranoside)propan-2-one,
1-(C-α-D-fucopyranoside)propan-2-one,
1-(C-β-L-fucopyranoside)propan-2-one,
1-(C-α-L-fucopyranoside)propan-2-one,
1-(C-β-D-fucopyranoside)-2-hydroxypropane,
1-(C-α-D-fucopyranoside)-2-hydroxypropane,
1-(C-β-L-fucopyranoside)-2-hydroxypropane,
1-(C-α-L-fucopyranoside)-2-hydroxypropane,
1-(C-β-D-glucopyranosyl)-2-hydroxypropane,
1-(C-α-D-glucopyranosyl)-2-hydroxypropane,
1-(C-β-D-galactopyranosyl)-2-hydroxypropane,
1-(C-α-D-galactopyranosyl)-2-hydroxypropane
1-(C-β-D-fucofuranosyl)propan-2-one,
1-(C-α-D-fucofuranosyl)propan-2-one
1-(C-β-L-fucofuranosyl)propan-2-one,
1-(C-α-L-fucofuranosyl)propan-2-one,
C-β-D-maltopyranoside-n-propan-2-one,
C-α-D-maltopyranoside-n-propan-2-one
C-β-D-maltopyranoside-2-hydroxypropane,
C-α-D-maltopyranoside-2-hydroxypropane, isomers thereof and mixtures thereof.

According to one embodiment, C-β-D-xylopyranoside-2-hydroxypropane or C-α-D-xylopyranoside-2-hydroxypropane, and better still C-β-D-xylopyranoside-2-hydroxypropane, may advantageously be used for the preparation of a composition according to the invention.

According to one particular embodiment, the C-glycoside derivative may be C-α-D-xylopyranoside-2-hydroxypropane in the form of a solution containing 30% of active material in a water/propylene glycol mixture (60%/40% by weight), such as the product manufactured by Chimex under the trade name Mexoryl SDB®.

Needless to say, according to the invention, a C-glycoside derivative corresponding to formula (I) may be used alone or as a mixture with other C-glycoside derivatives and in all proportions.

A C-glycoside derivative that is suitable for use in the invention may especially be obtained via the synthetic method described in document WO 02/051 828.

The amount of C-glycoside derivative to be used in a composition according to the invention depends on the desired cosmetic or therapeutic effect, and may thus vary within a wide range.

A person skilled in the art can readily determine the appropriate amounts, on the basis of his general knowledge.

A composition in accordance with the invention may comprise a C-glycoside derivative in a proportion of about from 0.0001% to about 25% by weight relative to the total weight of the composition, and in particular from about 0.001% to about 10% by weight and even more particularly between 0.05% and 5% by weight of C-glycoside derivative active material relative to the total weight of the composition.

Additives

The C-glycoside derivative(s) may be used in combination with other active agents.

Typically, according to one aspect of the invention, the C-glycoside derivative(s) may be used in combination with at least:

one moisturizing product,
one epidermal or dermal protease effector,
one enzyme and especially one exogenous protease and/or glycosidase and/or lipase, and/or
one active agent for improving epidermal differentiation, and/or
one anti-seborrhoeic agent.

The term "moisturizer" means;

either a compound that acts on the barrier function, in order to maintain the moisturization of the stratum corneum, or an occlusive compound. Mention may be made of ceramides, sphingoid-based compounds, lecithins, glycosphingolipids, phospholipids, cholesterol and derivatives thereof, phytosterols (stigmasterol, β-sitosterol or campesterol), essential fatty acids, 1,2-diacylglycerol, 4-chromanone, pentacyclic triterpenes such as ursolic acid, petroleum jelly and lanolin;

or a compound that directly increases the water content of the stratum corneum, such as trehalose and derivatives thereof, hyaluronic acid and derivatives thereof, glycerol, pentanediol, sodium pidolate, serine, xylitol, sodium lactate, polyglyceryl acrylate, ectoin and derivatives thereof, chitosan, oligosaccharides and polysacchardes, cyclic carbonates, N-lauroylpyrrolidonecarboxylic acid and N-α-benzoyl-L-arginine;

or a compound that activates the sebaceous glands, such as steroid derivatives (including DHEA) and vitamin D and derivatives thereof. This latter category of compounds will be more particularly suitable for application to mature skin, or even very mature skin, for example in the case of individuals more than 55 or 60 years old.

A urea derivative described especially in patent application DE-A-2 703 185 may especially be incorporated into the composition. Among these, N-(2-hydroxyethyl)urea is also commercially available, in the form of a mixture at 50% by weight in water, from the company National Starch under the trade name Hydrovance®.

These compounds may represent from 0.001% to 20% and preferably from 0.01% to 10% of the total weight of the composition according to the invention, and even more preferentially between 0.05% and 5% by weight relative to the total weight of the composition.

The use of at least one C-glycoside derivative in combination with at least one moisturizer mentioned above is advantageously intended for preventing or treating xerosis.

The expression "epidermal or dermal protease effector" means any molecule capable of inhibiting or activating enzymes via direct interactions (e.g.: protease inhibitors) or via indirect interactions with the substrates (e.g.: urea and urea derivatives), but also molecules capable of modulating the microenvironment of the enzyme (presence of effector salts, pH changes, etc.).

The term "effector" covers the possible use of protease inhibitors when certain activities are undesirable, such as the inhibitors of certain serine proteases (such as urokinase, chymotrypsins or trypsins) and metalloproteases. Specifically, it is known that certain enzymes have a deleterious effect on the constituents of the dermis or of the epidermis and their activity should be suppressed in order to obtain an optimum effect on the aspect and radiance of the skin.

The compositions according to the invention may also contain other enzymes and in particular exogenous proteases, and/or glycosidases and/or lipases and/or amidases. Such compounds are conventionally used in desquamating compositions and/or compositions for accelerating the renewal of the horny layer, and the combination of at least one C-glycoside compound as defined above will make it possible to reinforce and/or prolong their action.

The expression "exogenous proteases and/or glycosidases and/or lipases" means enzymes of recombinant origin or enzymes present in plant extracts, such as serine proteases, aspartic acid proteases, cysteine proteases or metalloproteases, glycosidases belonging to the family of exoglycosidases or endoglycosidases, and acidic or basic lipases.

The concentrations of these enzymes will be adapted according to the degree of purity and the activity of the product containing them. They are generally from 0.0001% to 5%, but may be lowered to concentrations of less than or equal to 1%, or even less than or equal to 0.1%, in combination with compounds of formula (I) according to the invention.

The term "active agent for improving epidermal differentiation" means an active agent capable of promoting and/or accelerating epidermal stratification resulting in a barrier function of better quality and/or an epidermal aspect of yellow skin type, especially with combating of the flattening of the dermo-epidermal junction.

Among these active agents, mention may be made of 8-hexadecene-1,16-dicarboxylic acid (dioic acid), vitamin D derivatives, ecdysterone and PPAR agonists, active agents for promoting the synthesis of epidermal glycosaminoglycans and proteoglycans such as Perlecan, histone deacetylase inhibitors, and growth factors or analogues thereof such as KGF or LIF.

The compositions according to the invention may also contain anti-seborrhoeic agents and, for example, a 5-α-reductase inhibitor; these agents may be chosen especially from:

retinoids, and in particular retinol;
sulfur and sulfur derivatives;
zinc salts such as zinc lactate, gluconate, pidolate, carboxylate, salicylate and/or cysteate;
selenium chloride;
vitamin 86 or pyridoxine;
the mixture of capryloyl glycine, sarcosine and extract of *Cinnamomum zeylanicum* sold especially by the company SEPPIC under the trade name Sepicontrol A5®;

an extract of *Laminaria saccharina* sold especially by the company Biotech Marine under the trade name Phlorogine®;

an extract of *Spiraea ulmaria* sold especially by the company Silab under the trade name Sebonormine®;

plant extracts from the species *Arnica montana, Cinchona succirubra, Eugenia caryophyllata, Humulus lupulus, Hypericum perfortaum, Mentha piperita, Rosmarinus officinalis, Salvia officinalis* and *Thymus vulgaris*, all sold, for example, by the company Maruzen;

an extract of *Serenoa repens* sold especially by the company Euromed;

plant extracts of the genus *Silybum*; and extracts of *Eugenia caryophyllata* containing eugenol and eugenyl glucoside.

The compositions containing such agents will be more particularly intended for treating greasy or hyperseborrhoeic skin.

A composition according to the invention may be for cosmetic and/or pharmaceutical use, and especially for dermatological use.

The compositions according to the invention comprise a physiologically acceptable vehicle, i.e. a medium that is compatible with any keratin material such as the skin, the scalp, the nails, mucous membranes, the eyes and the hair. According to one preferred embodiment of the invention, the composition has a pH close to that of the skin, of between 4 and 7.

The physiologically acceptable medium may comprise an aqueous phase, optionally as a mixture with one or more organic solvents such as a $C_1$-$C_8$ alcohol, especially ethanol, isopropanol, tert-butanol, n-butanol, polyols, for instance glycerol, propylene glycol, butylene glycol, and polyol ethers. It may also be anhydrous.

A composition according to the invention may also comprise a fatty phase, which may comprise oils, gums or waxes usually used in the field of application under consideration.

When the composition of the invention is an emulsion, the proportion of the fatty phase may range from 5% at 80% by weight and preferably from 5% to 50% by weight relative to the total weight of the composition.

The oils, waxes, emulsifiers and coemulsifiers used in the composition in emulsion form are chosen from those conventionally used in the field under consideration. The emulsifier and the coemulsifier are generally present in the composition in a proportion ranging from 0.3% to 30% by weight and preferably from 0.5% to 20% by weight relative to the total weight of the composition. The emulsion may also contain lipid vesicles.

As oils that may be used in the composition of the invention, examples that may be mentioned include:

hydrocarbon-based oils of animal origin, such as perhydrosqualene;

hydrocarbon-based oils of plant origin, such as liquid triglycerides of fatty acids containing from 4 to 10 carbon atoms and the liquid fraction of shea butter;

synthetic esters and synthetic ethers, especially of fatty acids, for instance oils of formulae $R_1COOR_2$, and $R_1OR_2$ in which $R_1$ represents a fatty acid residue containing from 8 to 29 carbon atoms and $R_2$ represents a branched or unbranched hydrocarbon-based chain containing from 3 to 30 carbon atoms, such as, for example, purcellin oil, isononyl isononanoate, isopropyl myristate, 2-ethylhexyl palmitate, 2-octyldodecyl stearate, 2-octyldodecyl erucate, isostearyl isostearate; hydroxylated esters such as isostearyl lactate, octyl hydroxystearate, octyldodecyl hydroxystearate, diisostearyl malate, triisocetyl citrate and fatty alkyl heptanoates, octanoates and decanoates; polyol esters, for instance propylene glycol dioctanoate, neopentyl glycol diheptanoate and diethylene glycol diisononanoate; and pentaerythritol esters, for instance pentaerythrityl tetraisostearate;

linear or branched hydrocarbons of mineral or synthetic origin, such as volatile or non-volatile liquid paraffins, and derivatives thereof, petroleum jelly, polydecenes, and hydrogenated polyisobutene such as parleam oil;

fatty alcohols containing from 8 to 26 carbon atoms, for instance cetyl alcohol, stearyl alcohol and a mixture thereof (cetylstearyl alcohol), octyldodecanol, 2-butyloctanol, 2-hexyldecanol, 2-undecylpentadecanol, oleyl alcohol or linoleyl alcohol;

partially hydrocarbon-based and/or silicone-based fluoro oils, for instance those described in document JP-A-2 295 912;

silicone oils, for instance volatile or non-volatile polymethylsiloxanes (PDMSs) containing a linear or cyclic silicone chain, that are liquid or pasty at room temperature, especially cyclopolydimethylsiloxanes (cyclomethicones) such as cyclohexasiloxane; polydimethylsiloxanes comprising alkyl, alkoxy or phenyl groups, which are pendent or at the end of a silicone chain, these groups containing from 2 to 24 carbon atoms; phenyl silicones, for instance phenyl trimethicones, phenyl dimethicones, phenyltrimethylsiloxydiphenylsiloxanes, diphenyl dimethicones, diphenylmethyldiphenyltrisiloxanes, 2-phenylethyltrimethyl siloxysilicates and polymethylphenylsiloxanes; and mixtures thereof.

As emulsifiers and coemulsifiers that may be used in the invention, examples that may be mentioned include O/W emulsifiers such as fatty acid esters of polyethylene glycol, especially PEG-100 stearate, and fatty acid esters of glycerol such as glyceryl stearate, and also W/O emulsifiers such as the oxyethylenated poly(methylcetyl)(dimethyl)methylsiloxane sold under the trade name Abil WE 09 by the company Degussa-Goldschmidt.

In a known manner, the composition according to the invention may also contain adjuvants that are common in cosmetics and dermatology, such as hydrophilic or lipophilic gelling agents, preserving agents, antioxidants, solvents, fragrances, fillers, screening agents, pigments, odour absorbers and dyestuffs. The amounts of these various adjuvants are those conventionally used in the field under consideration, for example from 0.01% to 20% of the total weight of the composition. Depending on their nature, these adjuvants may be introduced into the fatty phase, into the aqueous phase and/or into lipid spherules. In any case, these adjuvants, and the proportions thereof, will be chosen so as not harm the properties desired for the compound according to the invention.

Hydrophilic gelling agents that may be mentioned in particular include carboxyvinyl polymers (carbomer), acrylic copolymers such as acrylate/alkylacrylate copolymers, polyacrylamides, polysaccharides, natural gums and clays, and lipophilic gelling agents that may be mentioned include modified clays, for instance bentones, metal salts of fatty acids, hydrophobic silica and polyethylenes.

As fillers that may be used in the composition of the invention, besides pigments, examples that may be mentioned include silica powder; talc; starch crosslinked with octenylsuccinic anhydride, sold by the company National Starch under the name Dry-Flo Plus (28-1160); polyamide particles and especially those sold under the name Orgasol by the company Atochem; polyethylene powders; microspheres based on acrylic copolymers, such as those made of ethylene glycol dimethacrylate/lauryl methacrylate copolymer sold by the company Dow Corning under the name Polytrap; expanded powders such as hollow microspheres, and especially the microspheres sold under the name Expancel by the company Kemanord Plast or under the name Micropearl F 80 ED by the company Matsumoto; silicone resin microbeads such as those sold under the name Tospearl by the company Toshiba Silicone; and mixtures thereof. These fillers may be present in amounts ranging from 0 to 20% by weight and preferably from 1% to 10% by weight relative to the total weight of the composition according to the invention.

The compositions that may be used according to the invention may be ingested, injected or applied to the skin (to any area of bodily skin), the hair, the nails or mucous membranes (oral, jugal, gingival, genital or connective tissue membranes).

According to the adopted mode of administration, a composition according to the invention may be in any galenical form normally used, particularly in cosmetology. For obvious reasons, the amount of C-glycoside in the compositions according to the invention is liable to vary significantly as a function of the intended purpose of the composition and/or of its mode of administration.

In general, the C-glycoside derivative may be used in topical mode at a concentration of between 0.01% and 25% by weight and preferably between 0.5% and 20% by weight of active material relative to the total weight of the composition.

The compositions according to the invention are preferably formulated in a form that is suitable for topical administration.

When it is applied topically, the composition comprising at least one C-glycoside derivative may be applied to the face, the neck, the scalp, mucous membranes and the nails or to any other area of bodily skin.

The application times will vary as a function of the concentration of C-glycoside in the composition, and of the desired effect. As a guide, the composition may remain in contact with the skin or the integuments for between 5 minutes and 12 hours, and may optionally be removed after this contact time. The application may be performed daily or twice-daily, or weekly, and repeated for periods of 2 weeks to 6 months; this period may be prolonged or renewed without difficulty.

These compositions are especially in the form of aqueous, aqueous-alcoholic or oily solutions, dispersions of the lotion or serum type, anhydrous or oily gels, emulsions of liquid or semi-liquid consistency of the milk type, obtained by dispersing a fatty phase in an aqueous phase (O/W) or conversely (W/O), suspensions or emulsions of soft, semi-solid or solid consistency of the cream or gel type, microemulsions, or alternatively microcapsules, microparticles or vesicular dispersions of ionic and/or nonionic type. These compositions are prepared according to the usual methods.

The amounts of the various constituents of the compositions used according to the invention are those conventionally used in the fields under consideration.

These compositions especially constitute protective, treating or care creams for the face, the hands or the body, protective or care body milks, lotions, gels or mousses for caring for the skin and mucous membranes or for cleansing the skin, masks or patches.

The compositions may also consist of solid preparations constituting cleansing soaps or bars.

The compositions that may be used according to the invention may also be packaged in the form of an aerosol composition also comprising a pressurized propellant.

During topical application, the composition may be applied directly to the damaged area or to its vicinity, or alternatively, in the case of pathologies comprising crisis periods and rest periods, at a site bearing a lesion, as a preventive measure, to prolong a state of remission between two crises.

Thus, the invention also relates to the use of at least one C-glycoside derivative for the preparation of a composition for treating skin showing signs of deregulation of desquamation.

The compositions according to the invention are especially exfoliant compositions suitable for scrubbing rough areas from the skin. They may also be peeling compositions, for removing a larger thickness of horny layer such as corns.

Compositions according to the invention are also compositions intended for cleansing the skin and/or the scalp, in which the action of the cleansing agents will be reinforced by promoting the removal of dead cells from the cleansed surface.

According to yet another aspect of the invention, the composition containing the compound of formula (I) or derivatives thereof is a care composition for improving the surface condition of the skin and/or mucous membranes, especially the lips; in particular, the said composition will promote the removal of rough areas and/or dead skin present at the surface of the skin and/or the lips.

According to another embodiment of the invention, the compositions are intended for promoting cicatrization, by promoting the removal of adhesions.

The composition that may be used according to the invention may also be a haircare composition, especially a shampoo, a hairsetting lotion, a medicated lotion, a styling cream or gel, a dye composition (especially for oxidation dyeing) optionally in the form of colouring shampoos, restructuring lotions for the hair, a permanent-waving composition (especially a composition for the first stage of a permanent-waving operation), a composition for inducing and/or stabilizing natural hair loss in man, advantageously a lotion or gel, an antiparasitic shampoo, etc.

The invention is illustrated in greater detail in the examples that follow. These examples shall not in any way limit the scope of the invention.

EXAMPLE

Characterization of the Desquamating Activity of a C-Glycoside

The C-glycoside derivative used in the examples below is C-β-D-xylopyranoside-n-propane-2-one sold under the name Mexoryl SBB® by Chimex. It is in the form of a solution at 30% by weight of active material (AM) in a 60/40 water/1,2-propanediol mixture.

Principle of the Test:

In this test, corneodesmosine is sought by immunodetection after incubation. Corneodesmosine is one of the key markers of desquamation of corneodesmosines. It is studied on an immunoblot after electrophoresis separation and transfer onto a membrane. After specific labelling with the antibody G3619, it is revealed by chemiluminescence.

Materials and Methods:
Formulae Studied:

| Formula | Formula |
|---|---|
| Excipient (Arlacel/Myrj base) | 1 |
| C-β-D-xylopyranoside-2-hydroxypropane | 2 |
| Glycerol | 3 |

| Chemical Name | % by weight | | |
|---|---|---|---|
| | 1 | 2 | 3 |
| C-β-D-xylopyranoside-2-hydroxypropane (AM) | — | 7 | — |
| Triethanolamine | 0.3 | 0.3 | 0.3 |
| Propyl p-hydroxybenzoate | 0.1 | 0.1 | 0.1 |
| Methyl p-hydroxybenzoate | 0.2 | 0.2 | 0.2 |
| Cetyl alcohol | 1 | 1 | 1 |
| Stearyl alcohol | 1 | 1 | 1 |
| Hydrogenated isoparaffin (6-8 mol of isobutylene) (Parleam sold by NoF Corporation) | 5 | 5 | 5 |
| Carboxyvinyl polymer synthesized in an ethyl acetate/cyclohexane mixture (Carbopol 981, sold by Noveon) | 0.3 | 0.3 | 0.3 |
| Cyclopentadimethylsiloxane | 15 | 15 | 15 |
| Deionized water | qs 100 | qs 100 | qs 100 |
| Glycerol | — | — | 7 |
| Polyethylene (50 EO) glycol monostearate (Myrj 53P sold by Uniqema) | 2.5 | 2.5 | 2.5 |
| Glyceryl mono/distearate/polyethylene glycol (100 EO) stearate mixture (Arlacel 165 FL sold by Uniqema) | 2.5 | 2.5 | 2.5 |

AM: active material

Test Protocol:

3×3.5 cm rectangles are cut out of varnish strippings performed on the calf area of legs bearing dry skin. They are each treated with 42 mg of product (4 mg/cm$^2$). Controls and tests are performed in parallel. A blank without product is prepared under the same conditions.

The tests are incubated at 37° C. and 70% relative humidity for 5 days. The controls are stored for 5 days at −20° C. Thus, 5 tests and 5 controls are obtained.

For each of the samples, acetone powders are prepared and weighed out. The proteins are extracted with 100 μl/mg of whole Laemmli buffer. They are assayed according to the Bradford method. The protein content of each sample is adjusted and allows a direct comparison of the various samples. The proteins are separated by SDS-Page electrophoresis on 12% acrylamide gel.

After transferring the proteins onto a PVDF membrane, the immunodetection is performed with the anticorneodesmosine antibody G3619 (Guy Serre) at 1/12500 according to a standard western blot technique. Revelation is performed by chemiluminescence. The bands detected by the Fluor Smax machine (Biorad) are quantified with the quantity-one software (Biorad).

Results:

The results represent the quantification of the corneodesmosines.

Quantification of the corneodesmosine bands for each sample units: cnt*mm$^2$

| | Corneodesmosines | |
|---|---|---|
| | Control | Test |
| Formula 1 | 2198 | 2690 |
| Formula 2 | 2229 | 1192 |
| Formula 3 | 2748 | 904 |
| Blank | 1667 | 1710 |

The table below shows the percentage of residual corneodesmosines of the test relative to the control. The lower the percentage, the more the corneodesmosine is degraded.

| | % of residual corneodesmosines |
|---|---|
| Formula 1 | 122 |
| Formula 2 | 53 |
| Formula 3 | 33 |
| Blank | 103 |

The blank represents the "self-hydrolysis" of the corneodesmosine under the operating conditions of the test. No degradation of the corneodesmosine is observed for the blank.

The excipient (Arlacel/Myrj base) is a neutral support close to the blank without treatment.

Glycerol, which is the positive blank, shows substantial degradation of corneodesmosine. The C-β-D-xylopyranoside-2-hydroxypropane tested shows a positive effect in this test.

The invention claimed is:

1. A cosmetic method for promoting desquamation of the skin and/or the scalp comprising at least the topical administration to the skin and/or the scalp, as a cosmetic agent, of at least one C-glycoside derivative in a composition comprising a physiologically acceptable medium to promote desquamation to thereby treat xerosis, acne, hyperkeratosis, or ichthyosis, wherein the C-glycoside derivative corresponds to the general formula (I) below:

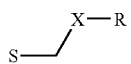

in which:
R represents:
   a linear $C_1$-$C_4$ radical, optionally substituted with —OH, —COOH or —COOR''$_2$,
   R''$_2$ being a saturated $C_1$-$C_4$ alkyl radical;
X represents a radical chosen from the groups:

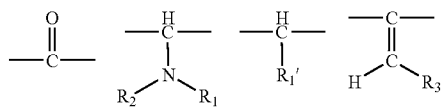

with $R_1$, $R_2$ and $R_3$ representing, independently of each other, a hydrogen atom or a radical R, with R as defined above, and $R_1'$ represents a hydrogen atom, an —OH group or a radical R as defined above, $R_1$ can also be a $C_6$-$C_{10}$ aryl radical;
S represents a monosaccharide or a polysaccharide comprising up to 20 sugar units, in pyranose and/or furanose form and of L and/or D series, the mono- or polysaccharide optionally being substituted with a mandatorily free hydroxyl group or one or more protected amine function(s), and
the bond S—CH$_2$—X represents a bond of C-anomeric nature, which is α or β,
   and also the cosmetically acceptable salts thereof, the solvates thereof and the isomers thereof, the C-glycoside derivative being present in a proportion of 0.05% to 10% by weight relative to the total weight of the composition.

2. A method for treating signs associated with a desquamation disorder comprising the topical administration to the skin and/or the scalp of at least one C-glycoside derivative to treat the signs associated with the desquamation disorder, wherein the desquamation disorder is selected from the group consisting of xerosis, acne, hyperkeratosis, and ichthyosis, and the C-glycoside derivative corresponds to the general formula (I) below:

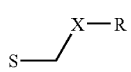

in which:
R represents:
   a linear $C_1$-$C_4$ radical, optionally substituted with —OH, —COOH or —COOR''$_2$,
   R''$_2$ being a saturated $C_1$-$C_4$ alkyl radical;
X represents a radical chosen from the groups:

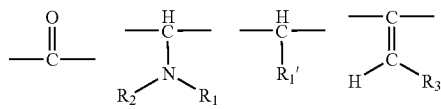

with $R_1$, $R_2$ and $R_3$ representing, independently of each other, a hydrogen atom or a radical R, with R as defined above, and $R_1'$ represents a hydrogen atom, an —OH group or a radical R as defined above, $R_1$ can also be a $C_6$-$C_{10}$ aryl radical;
S represents a monosaccharide or a polysaccharide comprising up to 20 sugar units, in pyranose and/or furanose form and of L and/or D series, the mono- or polysaccharide optionally being substituted with a mandatorily free hydroxyl group or one or more protected amine function(s), and
the bond S—CH$_2$—X represents a bond of C-anomeric nature, which is α or β,
   and also the cosmetically acceptable salts thereof, the solvates thereof and the isomers thereof.

3. The method according to claim 1, in which S represents a monosaccharide chosen from D-glucose, D-xylose, L-fucose, D-galactose and D-maltose.

4. The method according to claim 1, in which X represents a group chosen from —CO—, —CH(OH)— and —CH(NH$_2$)—.

5. The method according to claim 1, in which the C-glycoside derivative is chosen from:
   C-β-D-xylopyranoside-n-propan-2-one,
   C-α-D-xylopyranoside-n-propan-2-one,
   C-β-D-xylopyranoside-2-hydroxypropane,
   C-α-D-xylopyranoside-2-hydroxypropane,
   1-(C-β-D-fucopyranoside)propan-2-one,
   1-(C-α-D-fucopyranoside)propan-2-one,
   1-(C-β-L-fucopyranoside)propan-2-one,
   1-(C-α-L-fucopyranoside)propan-2-one,
   1-(C-β-D-fucopyranoside)-2-hydroxypropane,
   1-(C-α-D-fucopyranoside)-2-hydroxypropane,
   1-(C-β-L-fucopyranoside)-2-hydroxypropane,
   1-(C-α-L-fucopyranoside)-2-hydroxypropane,
   1-(C-β-D-glucopyranosyl)-2-hydroxylpropane,
   1-(C-α-D-glucopyranosyl)-2-hydroxylpropane,
   1-(C-β-D-galactopyranosyl)-2-hydroxylpropane,
   1-(C-α-D-galactopyranosyl)-2-hydroxylpropane
   1-(C-β-D-fucofuranosyl)propan-2-one,
   1-(C-α-D-fucofuranosyl)propan-2-one
   1-(C-β-L-fucofuranosyl)propan-2-one,
   1-(C-α-L-fucofuranosyl)propan-2-one,
   C-β-D-maltopyranoside-n-propan-2-one,
   C-α-D-maltopyranoside-n-propan-2-one
   C-β-D-maltopyranoside-2-hydroxypropane,
   C-α-D-maltopyranoside-2-hydroxypropane, isomers thereof and mixtures thereof.

6. The method according to claim 1 in which the C-glycoside derivative is chosen from C-β-D-xylopyranoside-2-hydroxypropane and C-α-D-xylopyranoside-2-hydroxypropane.

7. The method according to claim 1, in which the C-glycoside derivative is used in combination with at least:
   one moisturizing product,
   one epidermal or dermal protease effector,
   one exogenous protease and/or glycosidase and/or lipase,
   one active agent for improving epidermal differentiation, and/or
   one anti-seborrhoeic agent.

8. A cosmetic treatment process for promoting desquamation, comprising at least the topical administration to the skin and/or the scalp of a composition comprising, in a physiologically acceptable medium, at least one C-glycoside derivative to promote desquamation to thereby treat xerosis, acne, hyperkeratosis, or ichthyosis, wherein the C-glycoside derivative corresponds to the general formula (I) below:

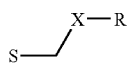

in which:
R represents:
a saturated $C_1$-$C_{20}$ or unsaturated $C_2$-$C_{20}$ linear alkyl radical, or a saturated or unsaturated, branched or cyclic $C_3$-$C_{20}$ alkyl radical;
a saturated $C_1$-$C_{20}$ or unsaturated $C_2$-$C_{20}$ linear, or saturated or unsaturated, branched or cyclic $C_3$-$C_{20}$ hydrofluoroalkyl or perfluoroalkyl radical;
the hydrocarbon-based chain constituting the radicals optionally being, where appropriate, interrupted with 1, 2, 3 or more heteroatoms chosen from:
an oxygen,
a sulfur,
a nitrogen, and
a silicon,
and being optionally substituted with at least one radical chosen from:
—$OR_4$,
—$SR_4$,
—$NR_4R_5$,
—$COOR_4$,
—$CONHR_4$,
—$CN$,
a halogen atom,
a $C_1$-$C_6$ hydrofluoroalkyl or perfluoroalkyl radical, and/or a $C_3$-$C_8$ cycloalkyl radical,
with $R_4$ and $R_5$ representing, independently of each other, a hydrogen atom or a saturated $C_1$-$C_{30}$ or unsaturated $C_2$-$C_{30}$ linear, or a saturated or unsaturated, branched or cyclic $C_3$-$C_{30}$ alkyl, perfluoroalkyl or hydrofluoroalkyl radical;
or a $C_6$-$C_{10}$ aryl radical;
X represents a radical chosen from the groups:

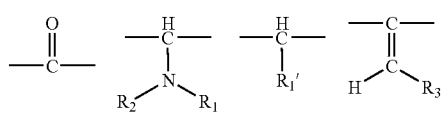

with $R_1$, $R_2$ and $R_3$ representing, independently of each other, a hydrogen atom or a radical R, with R as defined above, and $R_1'$ represents a hydrogen atom, an —OH group or a radical R as defined above, $R_1$ can also be a $C_6$-$C_{10}$ aryl radical;
S represents a monosaccharide or a polysaccharide comprising up to 20 sugar units, in pyranose and/or furanose form and of L and/or D series, the mono- or polysaccharide optionally being substituted with a mandatorily free hydroxyl group or one or more protected amine function(s), and
the bond S—$CH_2$—X represents a bond of C-anomeric nature, which is α or β,
and also the cosmetically acceptable salts thereof, the solvates thereof and the isomers thereof, the C-glycoside derivative being present in a proportion of 0.05% to 10% by weight relative to the total weight of the composition.

9. A method to promote regular desquamation of reconstructed skin comprising at least the topical administration to the reconstructed skin of a composition comprising, in a physiologically acceptable medium, at least one C-glycoside derivative to promote regular desquamation of the reconstructed skin, wherein the C-glycoside derivative corresponds to the general formula (I) below:

in which:
R represents:
a linear $C_1$-$C_4$ radical, optionally substituted with —OH, —COOH or —$COOR''_2$,
$R''_2$ being a saturated $C_1$-$C_4$ alkyl radical;
X represents a radical chosen from the groups:

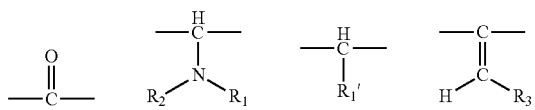

with $R_1$, $R_2$ and $R_3$ representing, independently of each other, a hydrogen atom or a radical R, with R as defined above, and $R_1'$ represents a hydrogen atom, an —OH group or a radical R as defined above, $R_1$ can also be a $C_6$-$C_{10}$ aryl radical;
S represents a monosaccharide or a polysaccharide comprising up to 20 sugar units, in pyranose and/or furanose form and of L and/or D series, the mono- or polysaccharide optionally being substituted with a mandatorily free hydroxyl group or one or more protected amine function(s), and
the bond S—$CH_2$—X represents a bond of C-anomeric nature, which is α or β, and also the cosmetically acceptable salts thereof, the solvates thereof and the isomers thereof, the C-glycoside derivative being present in a proportion of 0.05% to 10% by weight relative to the total weight of the composition.

* * * * *